United States Patent
Chao et al.

(10) Patent No.: US 9,893,304 B2
(45) Date of Patent: Feb. 13, 2018

(54) ORGANIC METAL COMPLEXES AND ORGANIC ELECTROLUMINESCENT DEVICES COMPRISING THE SAME

(71) Applicant: INDUSTRIAL TECHNOLOGY RESEARCH INSTITUTE, Hsinchu (TW)

(72) Inventors: Teng-Chih Chao, Hsinchu (TW); Meng-Hao Chang, New Taipei (TW); Han-Cheng Yeh, Taipei (TW); Ching-Hui Chou, Hsinchu (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 520 days.

(21) Appl. No.: 14/279,948

(22) Filed: May 16, 2014

(65) Prior Publication Data

US 2015/0188059 A1    Jul. 2, 2015

(30) Foreign Application Priority Data

Dec. 26, 2013  (TW) .............. 102148379 A

(51) Int. Cl.
| | | |
|---|---|---|
| H01L 51/54 | (2006.01) | |
| C09K 11/06 | (2006.01) | |
| H01L 51/00 | (2006.01) | |
| C07F 15/00 | (2006.01) | |
| H01L 51/50 | (2006.01) | |

(52) U.S. Cl.
CPC ...... *H01L 51/0085* (2013.01); *C07F 15/0033* (2013.01); *C09K 11/06* (2013.01); *C09K 2211/1029* (2013.01); *C09K 2211/1037* (2013.01); *C09K 2211/185* (2013.01); *H01L 51/0037* (2013.01); *H01L 51/5016* (2013.01); *H01L 2251/308* (2013.01)

(58) Field of Classification Search
None
See application file for complete search history.

(56) References Cited

U.S. PATENT DOCUMENTS

| | | |
|---|---|---|
| 7,445,857 B2 | 11/2008 | Shen et al. |
| 7,781,077 B2 | 8/2010 | Yang et al. |
| 7,790,888 B2 | 9/2010 | Bold et al. |
| 8,324,800 B2 | 12/2012 | Royster, Jr. et al. |
| 8,431,243 B2 | 4/2013 | Kwong et al. |
| 2003/0068536 A1 | 4/2003 | Tsuboyama et al. |
| 2007/0237981 A1 | 10/2007 | Shen et al. |
| 2011/0234089 A1* | 9/2011 | Hou et al. ............ C07D 277/66 313/504 |
| 2011/0285275 A1 | 11/2011 | Huang et al. |
| 2012/0061654 A1 | 3/2012 | Rayabarapu et al. |
| 2013/0033171 A1 | 2/2013 | Huang et al. |
| 2013/0033172 A1 | 2/2013 | Huang et al. |

FOREIGN PATENT DOCUMENTS

| | | |
|---|---|---|
| CN | 1803970 A | 7/2006 |
| CN | 102227438 A | 10/2011 |
| CN | 102911211 A | 2/2013 |
| CN | 102952162 A | 3/2013 |
| TW | I242999 B | 11/2005 |
| TW | I310051 | 5/2009 |
| TW | I348878 | 9/2011 |
| TW | 201141987 A1 | 12/2011 |
| TW | I395804 B1 | 5/2013 |

OTHER PUBLICATIONS

Taiwanese Office Action and Search Report dated Jan. 22, 2015, for Taiwanese Application No. 102148378.
Taiwanese Office Action and Search Report dated Jan. 22, 2015, for Taiwanese Application No. 102148379.
Huang et al., "Uniform dispersion of triplet emitters in multi-layer solution-processed organic light-emitting diodes", Synthetic Metals, vol. 160, 2010, pp. 2393-2396.
Peng et al., "Highly efficient phosphorescent OLEDs with host-independent and concentration-insensitive properties based on a bipolar iridium complex", Journal of Materials Chemistry C, vol. 1, Feb. 27, 2013, pp. 2920-2926.
Peng et al., "Very high-efficiency red-electroluminescence devices based on an amidinate-ligated phosphorescent iridium complex", Journal of Materials Chemistry, vol. 19, Oct. 12, 2009, pp. 8072-8074.
Son et al., "Small single-triplet energy gap bipolar host materials for phosphorescent blue and white organic light emitting diodes", Journal of Materials Chemistry C, vol. 1, No. 33, Jul. 22, 2013, pp. 5008-5014.

(Continued)

*Primary Examiner* — Marie R. Yamnitzky
(74) *Attorney, Agent, or Firm* — Birch, Stewart, Kolasch & Birch, LLP

(57) ABSTRACT

An organic metal complex and an organic electroluminescent device including the same are provided. The organic metal complex is represented by the formula of

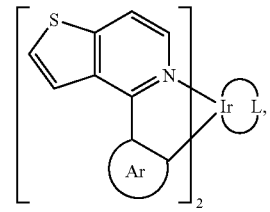

wherein Ar includes 1-naphthyl, 2-naphthyl or benzothienyl, and L includes acetylacetone, N,N-diisopropyl-benzamidinate or N,N-diisopropyl-diisopropyl-guanidinate. The organic electroluminescent device includes a pair of electrodes and an electroluminescent element disposed between the pair of electrodes, wherein the electroluminescent element includes the organic metal complex.

6 Claims, 1 Drawing Sheet

(56) References Cited

OTHER PUBLICATIONS

Yeh et al., "All-small-molecule efficient white organic light-emitting diodes by multi-layer blade coating", Organic Electronics, vol. 13, 2012, pp. 914-918.
Chinese Office Action for Appl. No. 201410122968.1 dated Nov. 28, 2016.
U.S. Office Action for U.S. Appl. No. 14/279,987 dated Jun. 7, 2017.
Zhao, Q., et al, "Synthesis and Photophysical, Electrochemical, and Electrophosphorescent Properties of a Series of Iridium(III) Complexes Based on Quinoline Derivatives and Different beta-Diketonate Ligands," Organometallics, Jun. 14, 2006, vol. 25, pp. 3631-3638.

* cited by examiner

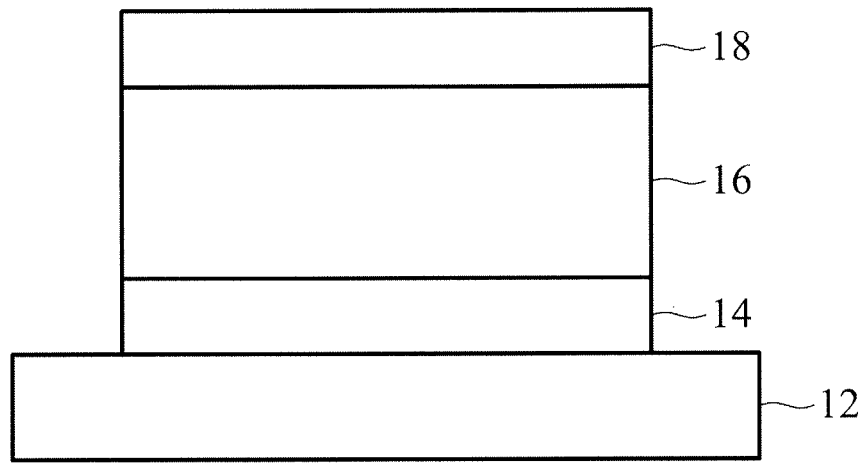

ORGANIC METAL COMPLEXES AND ORGANIC ELECTROLUMINESCENT DEVICES COMPRISING THE SAME

CROSS REFERENCE TO RELATED APPLICATIONS

This Application claims priority of Taiwan Patent Application No. 102148379, filed on Dec. 26, 2013, the entirety of which is incorporated by reference herein. The subject matter of this application relates to that of copending application Ser. No. 14/279,987 filed May 16, 2014 for "Organometallic compounds and organic electroluminescence devices employing the same" by Teng-Chih Chao, Meng-Hao Chang, Han-Cheng Yeh and Ching-Hui Chou. The disclosure of the copending application is incorporated herein by reference in their entirety.

TECHNICAL FIELD

The technical field relates to an organic metal complex and an organic electroluminescent device including the same.

BACKGROUND

Organic electroluminescent devices have superior characteristics, such as low driving voltage (e.g., 10V or less), broad viewing angle, rapid response time and high contrast, over liquid crystal displays (LCDs), plasma display panels (PDPs) and inorganic electroluminescent display devices. Based on these advantages, organic electroluminescent devices can be used as pixels of graphic displays, television image displays and surface light sources. In addition, organic electroluminescent devices can be fabricated on transparent flexible substrates, which can reduce the thickness and weight thereof and have good color representation. Therefore, in recent years, organic electroluminescent devices have gradually been used in flat panel displays (FPDs).

A representative organic electroluminescent device was reported by Gurnee in 1969 (U.S. Pat. Nos. 3,172,862 and 3,173,050). However, this organic electroluminescent device suffers from limitations in its applications because of its limited performance. Since Eastman Kodak Co. reported multilayer organic electroluminescent devices capable of overcoming the problems of prior-art devices in 1987, remarkable progress has been made in the development of the organic electroluminescent technique.

Such organic electroluminescent devices comprise a first electrode as a hole injection electrode (anode), a second electrode as an electron injection electrode (cathode), and an organic light-emitting layer disposed between the cathode and the anode, wherein holes injected from the anode and electrons injected from the cathode combine with each other in the organic light-emitting layer to form electron-hole pairs (excitons), and then the excitons fall from the excited state to the ground state and decay to emit light. At this time, the excitons may fall from the excited state to the ground state via the singlet excited state to emit light (i.e. fluorescence), or the excitons may fall from the excited state to the ground state via the triplet excited state to emit light (i.e. phosphorescence). In the case of fluorescence, the probability of the singlet excited state is 25% and thus the luminescence efficiency of the devices is limited. In contrast, phosphorescence can utilize both probabilities of the triplet excited state (75%) and the singlet excited state (25%), and thus the theoretical internal quantum efficiency may reach 100%. Therefore, it is crucial to develop highly efficient phosphorescent material, in order to increase the emissive efficiency of an organic electroluminescent device.

Currently, the main luminescent materials of the organic electroluminescent devices are small-molecule materials due to higher efficiency, brightness and life-span of the small-molecule organic electroluminescent devices than the polymer light-emitting diodes (PLEDs). A small-molecule organic electroluminescent device is mainly fabricated by way of vacuum evaporation rather than spin coating or inkjet printing like PLEDs. However, the equipment cost of the vacuum evaporation is high. Additionally, 95% of the organic electroluminescent materials are deposited on the chamber wall of the manufacturing equipment, such that only 5% of the organic electroluminescent materials are coated on a substrate, resulting in high manufacturing cost. Therefore, a wet process (such as spin coating or blade coating) has been provided to fabricate small-molecule organic electroluminescent devices to reduce equipment costs and improve the utilization rate of organic electroluminescent materials.

Therefore, for the organic electroluminescent technique, it is necessary to develop soluble organic phosphorescent materials which are suitable for use in a wet process.

SUMMARY

An exemplary embodiment of an organic metal complex has a chemical structure as represented by formula (I):

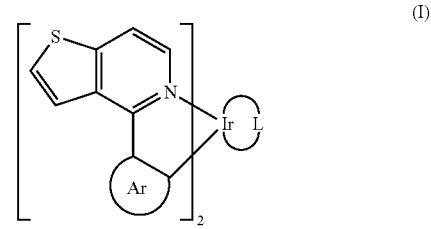

In formula (I), Ar comprises 1-naphthyl, 2-naphthyl or benzothienyl, and L comprises acetylacetone, N,N-diisopropyl-benzamidinate or N,N-diisopropyl-diisopropyl-guanidinate.

In another exemplary embodiment of the disclosure, an organic electroluminescent device is provided. The device comprises a pair of electrodes and an electroluminescent element disposed between the pair of electrodes, wherein the electroluminescent element comprises the organic metal complex represented by the aforementioned formula (I) (serving as a reddish orange or red phosphorescence dopant material).

An exemplary embodiment of an organic metal complex has a chemical structure as represented by formula (II):

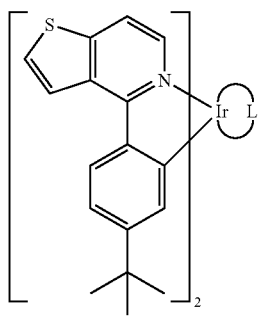

In formula (II), L comprises N,N-diisopropyl-diisopropyl-guanidinate.

In another exemplary embodiment of the disclosure, an organic electroluminescent device is provided. The device comprises a pair of electrodes and an electroluminescent element disposed between the pair of electrodes, wherein the electroluminescent element comprises the organic metal complex represented by the aforementioned formula (II) (serving as a reddish orange or red phosphorescence dopant material).

A detailed description is given in the following embodiments with reference to the accompanying drawings.

BRIEF DESCRIPTION OF THE DRAWINGS

The disclosure can be more fully understood by reading the subsequent detailed description and examples with references made to the accompanying drawings, wherein:

The FIGURE shows a cross-sectional view of an organic electroluminescent device disclosed by an embodiment of the disclosure.

DETAILED DESCRIPTION

The following description is of the best-contemplated mode of carrying out the disclosure. This description is made for the purpose of illustrating the general principles of the disclosure and should not be taken in a limiting sense. The scope of the disclosure is best determined by reference to the appended claims.

The disclosure provides an organic metal complex represented by the following formula (I):

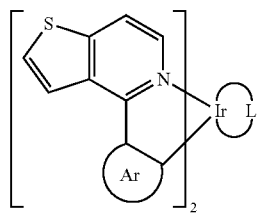

In formula (I), Ar may comprise 1-naphthyl, 2-naphthyl or benzothienyl, and L may comprise acetylacetone, N,N-diisopropyl-benzamidinate or N,N-diisopropyl-diisopropyl-guanidinate.

The disclosure provides an organic metal complex represented by the following formula (II):

(II)

In formula (II), L may comprise N,N-diisopropyl-diisopropyl-guanidinate.

The organic metal complexes represented by formula (I) or (II) acquired from a series of embodiments of the disclosure are shown in Table 1. The chemical structures thereof are shown in Table 1. In addition, the contractions thereof are also named and shown in Table 1.

TABLE 1

| Examples | Compound structures | Contraction |
| --- | --- | --- |
| 1 | 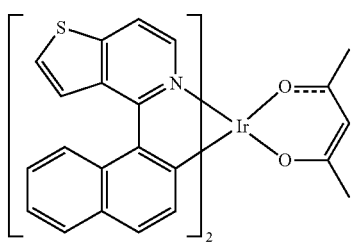 | PO-01-Np1-acac |

TABLE 1-continued

| Examples | Compound structures | Contraction |
|---|---|---|
| 2 | 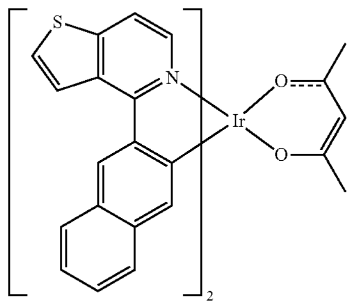 | PO-01-Np2-acac |
| 3 | 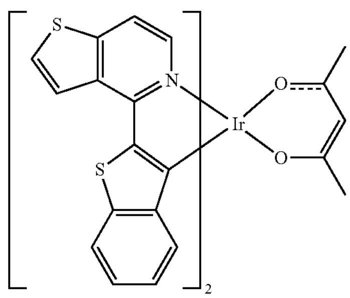 | PO-01-Bt-acac |
| 4 | 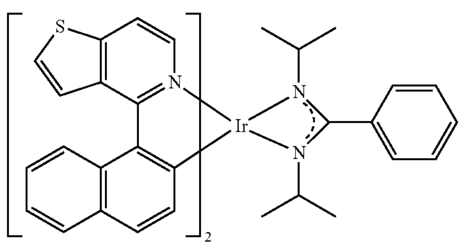 | PO-01-Np1-dipba |
| 5 | 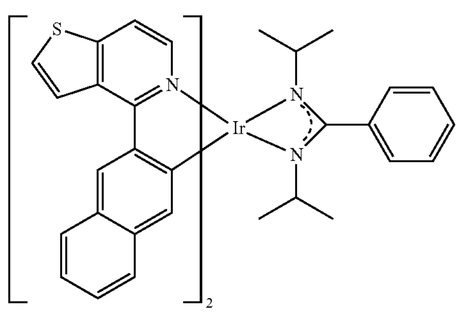 | PO-01-Np2-dipba |
| 6 | 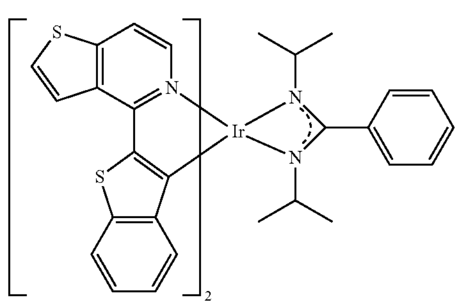 | PO-01-Bt-dipba |

TABLE 1-continued

| Examples | Compound structures | Contraction |
|---|---|---|
| 7 | 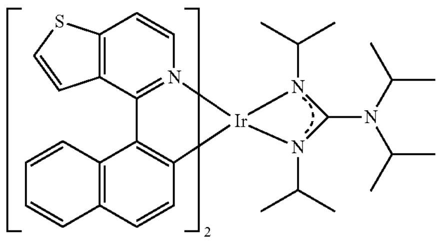 | PO-01-Np1-dipig |
| 8 | 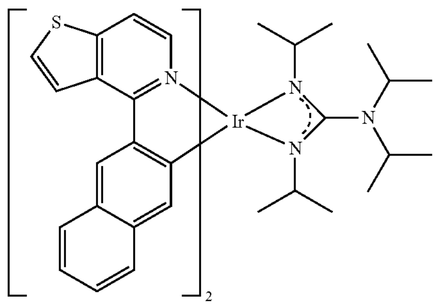 | PO-01-Np2-dipig |
| 9 | 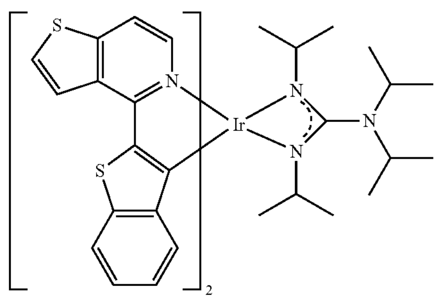 | PO-01-Bt-dipig |
| 10 | 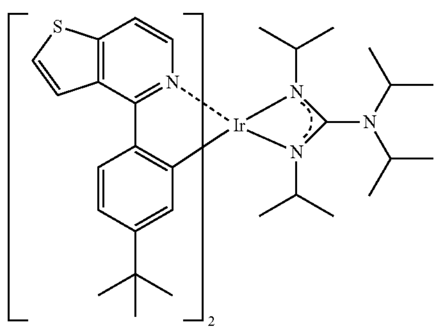 | PO-01-TB-dipig |

The FIGURE shows a cross-sectional view of an organic electroluminescent device 10 disclosed by an embodiment of the disclosure. Referring to the FIGURE, the organic electroluminescent device 10 comprises a substrate 12, a bottom electrode 14, an electroluminescent element 16, and a top electrode 18. The organic electroluminescent device 10 may be top-emission, bottom-emission, or dual-emission organic electroluminescent device. The substrate 12 may be a glass, plastic, or semiconductor substrate. Suitable materials for the bottom electrode 14 and the top electrode 18 may be Li, Mg, Ca, Al, Ag, In, Au, W, Ni, Pt, Cu, indium tin oxide (ITO), indium zinc oxide (IZO), aluminum zinc oxide (AZO), zinc oxide (ZnO) or combinations thereof, formed by, for example, thermal evaporation, sputtering, or plasma enhanced chemical vapor deposition (PECVD). Furthermore, at least one of the bottom electrode 14 and the top electrode 18 is transparent.

The electroluminescent element 16 comprises at least one emission layer, and may further comprise a hole injection layer, a hole transport layer, an electron transport layer, an electron injection layer or other layers. Specifically, in accordance with an embodiment of the disclosure, the electroluminescent element 16 comprises organic metal complexes having formula (I) or (II). That is, in the electroluminescent element 16, at least one layer comprises the aforementioned organic metal complexes.

According to another embodiment of the disclosure, the organic electroluminescent device 10 may be a phosphorescent organic electroluminescent device, and the phosphorescent electroluminescent element comprises a host material and a phosphorescent dopant material. The phosphorescent dopant material comprises the aforementioned organic metal complexes having formula (I) or (II).

One of ordinary skill in the art may dope the disclosed organic metal complexes and the required phosphorescent dopant materials and alter the doping amount of the adopted dopants based on the used organic electroluminescent material and the required characteristics of the device. Therefore, the doping amount of the dopants is neither related to the characteristic of the disclosure nor the base of limiting the scope of the disclosure.

In the disclosure, a substituent group with long conjugation length such as 1-naphthyl, 2-naphthyl or benzothienyl is conducted into the structure of the dopant material to reduce the energy gap between HOMO/LUMO of the material. Furthermore, the third auxiliary ligand (L) with low bandgap is adopted to shift the light color of the material from orange to red, remaining high luminous efficiency, simultaneously. In addition to adjusting the light color, the volatility and solubility of the material are also increased by conducting the substituent group such that the series of material is compatible with conventional vacuum deposition and solution processes.

Additionally, in the disclosure, few synthetic steps (five steps) are required, high yield (greater than 50%) is achieved, no isomers are formed, the molecular weight of the material is moderate (Mw. 700-900), purification of the product is simple, the material is inclined to sublimation (sublimation temperature less than 280° C.), the light color emitted from the material is adjustable (ranging from orange to red (i.e. 580-620 nm)), and the material is applied to deposition and solution processes without modification to fabricate device. The performance of the device prepared by the disclosed material through the deposition and solution processes is superior to that of the device prepared by the commodity materials.

Organic Metal Complexes

Example 1

Preparation of the Organic Metal Complex
(PO-01-Np1-acac, Ar=1-naphthyl)

Step 1:

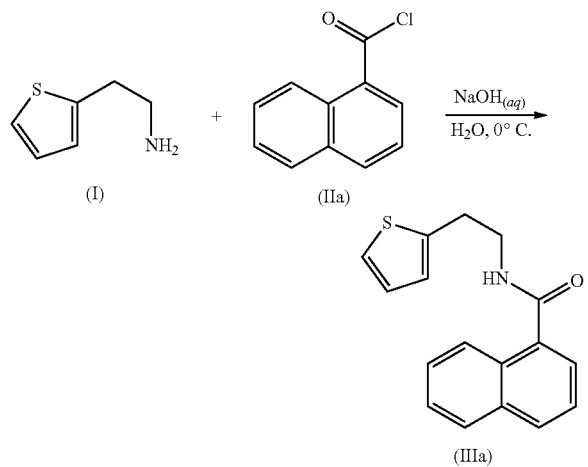

Compound (IIa) (1-naphthoyl chloride, 25 g, 131.14 mmol) and 150 mL of H$_2$O were added into a 500 mL single-neck bottle with an addition funnel. Next, compound (I) (2-(2-aminoethyl)thiophene, 20.09 g, 157.37 mmol, 1.2 eq.) was added dropwisely into the bottle via the addition funnel under ice-bath cooling. White solid was gradually formed. After dripping, a NaOH aqueous solution (20%) was added into the bottle and stirred overnight. After filtration with a porcelain funnel, a white solid of compound (IIIa) (23.2 g, yield of 63%) was obtained.

Step 2:

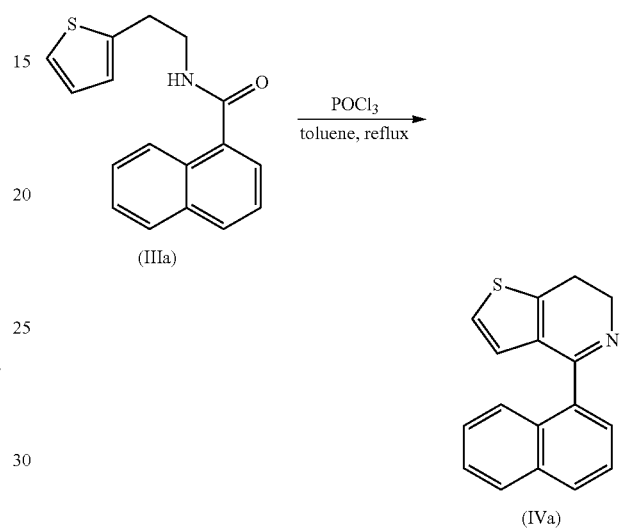

Compound (IIIa) (12 g, 42.7 mmol) and toluene (175 mL) were added into a 500 mL single-neck round-bottom flask. POCl$_3$ (12 mL, 128.1 mmol, 3 eq.) was added dropwisely into the flask via an addition funnel under ice-bath cooling. After dripping, the ice-bath was replaced by an oil bath and heated until toluene reflux. After reaction for two hours, a saturated NaHCO$_3$ aqueous solution was added into the flask for neutralization of the reaction. After toluene extraction, a toluene solution was collected and moisture was removed. After evaporation and standing for several hours, compound (IVa) (crystal, 10.5 g) was obtained with a yield of 93%.

Step 3:

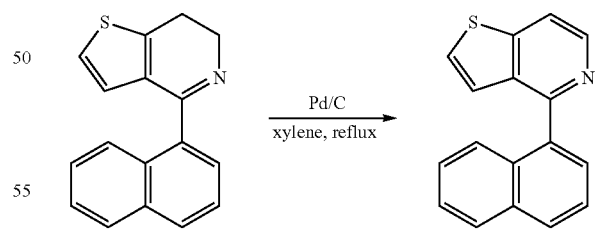

Compound (IVa) (8.4 g, 31.94 mmol), xylene (100 mL) and 10% Pd/C (15 g) were added into a 250 mL single-neck round-bottom flask and heated to xylene reflux. After reaction for 48 hours, the result was filtrated by diatomaceous earth (Celite 545) to remove Pd/C. After filtration, the filtrate was concentrated and purified by column chromatography (ethyl acetate/n-hexane=1/5), compound (Va) (5.8 g) was obtained with a yield of 70%.

Step 4:

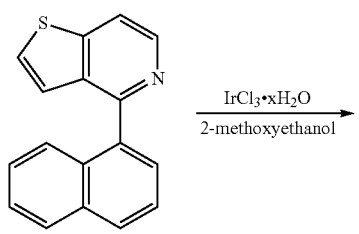

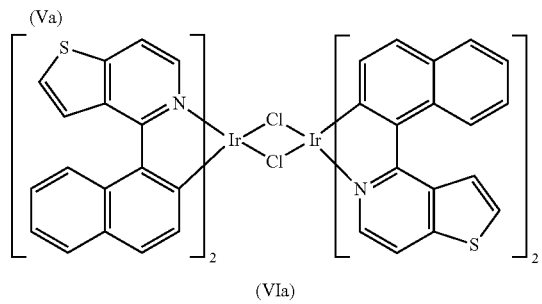

Compound (Va) (5 g, 19.14 mmol, 2.2 eq.), IrCl₃xH₂O (2.6 g, 8.7 mmol), 2-methoxy ethanol (21 mL), and water (7 mL) were added into a 100 mL single-neck round-bottom flask. After heating to 140° C. and reacting for 24 hours, the reaction was quenched by adding plenty of water. After filtration, compound (VIa) (dark red solid, 5.2 g) was obtained with a yield of 40%.

Step 5:

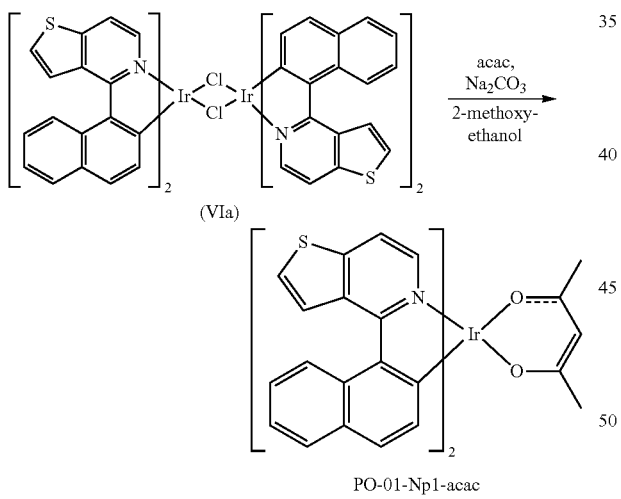

Compound (VIa) (5.0 g, 3.34 mmol), acetyl acetone (1.03 g, 10.28 mmol, 4 eq.), Na₂CO₃ (1.09 g, 10.28 mmol, 4 eq.), and 2-methoxyethanol (30 mL) were added into a 100 mL single-neck round-bottom flask and heated to 140° C. After reacting for 24 hours and cooling to room temperature, the result was washed with 50 mL water and filtered to obtain orange solid product. The product was purified by column chromatography with dichloromethane/n-hexane (1/1), obtaining compound (PO-01-Np1-acac) (orange solid product, 2.86 g) with a yield of 53%.

Compound (PO-01-Np1-acac) was analyzed by NMR spectroscopy. The spectral information of compound (PO-01-Np1-acac) is listed below:

¹H NMR (200 MHz, CDCl₃) δ 8.39 (d, J=6.2 Hz, 2H), 8.05 (d, J=8.4 Hz, 2H), 7.74 (t, J=6.2 Hz, 5H), 7.59 (d, J=6.8 Hz, 2H), 7.51 (d, J=5.6 Hz, 3H), 7.18-7.34 (m, 4H), 7.04 (d, J=8.1 Hz, 2H), 5.26 (s, 1H), 1.73 (s, 6H).

Example 2

Preparation of the Organic Metal Complex (PO-01-Np2-acac, Ar=2-naphthyl)

Step 1:

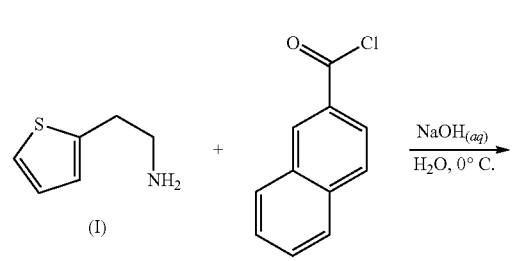

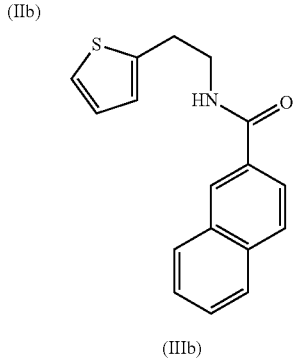

Compound (IIb) (2-naphthoyl chloride, 25 g, 131.14 mmol) and 150 mL of H₂O were added into a 500 mL single-neck bottle with an addition funnel. Next, compound (I) (2-(2-aminoethyl)thiophene, 20.09 g, 157.37 mmol, 1.2 eq.) was added dropwisely into the bottle via the addition funnel under ice-bath cooling. White solid was gradually formed. After dripping, a NaOH aqueous solution (20%) was added into the bottle and stirred overnight. After filtration with a porcelain funnel, a white solid of compound (IIIb) (29.5 g, yield of 80%) was obtained.

Step 2:

-continued

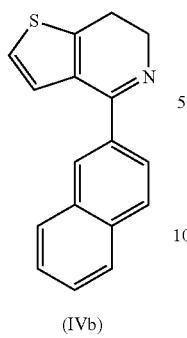

(IVb)

Compound (IIIb) (12 g, 42.7 mmol) and toluene (175 mL) were added into a 500 mL single-neck round-bottom flask. POCl$_3$ (12 mL, 128.1 mmol, 3 eq.) was added dropwisely into the flask via an addition funnel under ice-bath cooling. After dripping, the ice-bath was replaced by an oil bath and heated until toluene reflux. After reaction for two hours, a saturated NaHCO$_3$ aqueous solution was added into the flask for neutralization of the reaction. After toluene extraction, a toluene solution was collected and moisture was removed. After evaporation and standing for several hours, compound (IVb) (crystal, 9 g) was obtained with a yield of 80%.

Step 3:

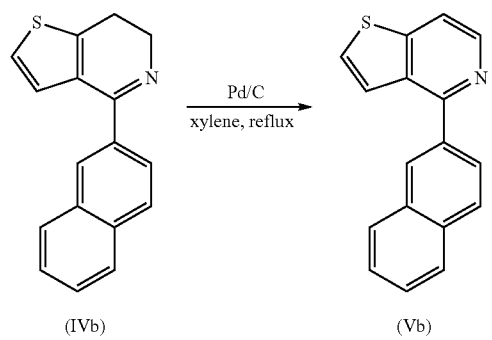 [SMILES: c1ccc2cc(C3=NCCc4sccc43)ccc2c1 ; c1ccc2cc(-c3nccc4sccc34)ccc2c1]

Compound (IVb) (9 g, 34.2 mmol), xylene (100 mL) and 10% Pd/C (15 g) were added into a 250 mL single-neck round-bottom flask and heated to xylene reflux. After reaction for 48 hours, the result was filtrated by diatomaceous earth (Celite 545) to remove Pd/C. After filtration, the filtrate was concentrated and purified by column chromatography (ethyl acetate/n-hexane=1/5), compound (Vb) (8.2 g) was obtained with a yield of 91%.

Step 4:

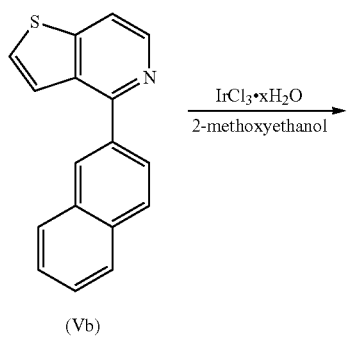

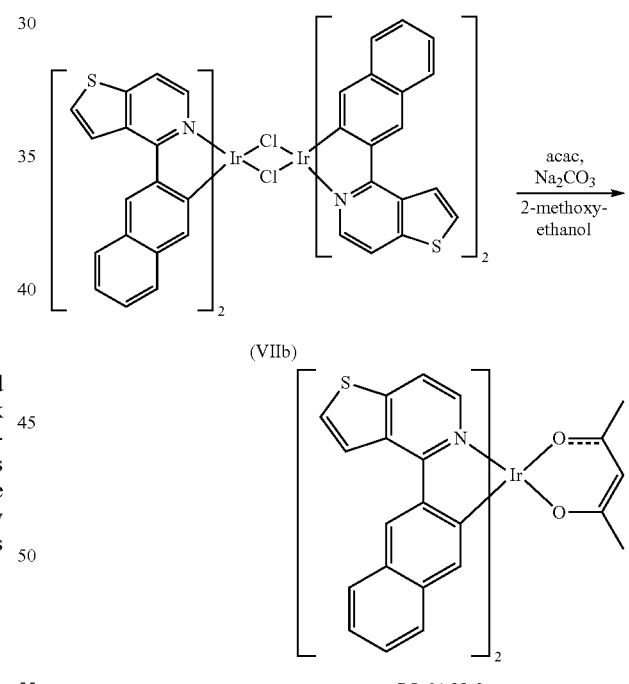

Compound (Vb) (5 g, 19.14 mmol, 2.2 eq.), IrCl$_3$·xH$_2$O (2.6 g, 8.7 mmol), 2-methoxy ethanol (21 mL), and water (7 mL) were added into a 100 mL single-neck round-bottom flask. After heating to 140° C. and reacting for 24 hours, the reaction was quenched by adding plenty of water. After filtration, compound (VIb) (orange solid, 6 g) was obtained with a yield of 46%.

Step 5:

Compound (VIb) (5.0 g, 3.34 mmol), acetyl acetone (1.61 g, 16.05 mmol, 4 eq.), Na$_2$CO$_3$ (1.7 g, 16.05 mmol, 4 eq.), and 2-methoxyethanol (30 mL) were added into a 100 mL single-neck round-bottom flask and heated to 140° C. After reacting for 24 hours and cooling to room temperature, the result was washed with 50 mL water and filtered to obtain orange solid product. The product was purified by column chromatography with dichloromethane/n-hexane (1/1), obtaining compound (PO-01-Np2-acac) (orange solid product, 2.70 g) with a yield of 50%.

Compound (PO-01-Np2-acac) was analyzed by NMR spectroscopy. The spectral information of compound (PO-01-Np2-acac) is listed below:

$^1$H NMR (200 MHz, CDCl$_3$) δ 8.69 (2, 2H), 8.61 (d, J=2.4 Hz, 4H), 7.76-7.90 (m, 6H), 7.01-7.19 (m, 6H), 6.64 (s, 2H), 5.26 (s, 1H), 1.76 (s, 6H).

Example 3

Preparation of the Organic Metal Complex (PO-01-Bt-acac, Ar=benzothienyl)

Step 1:

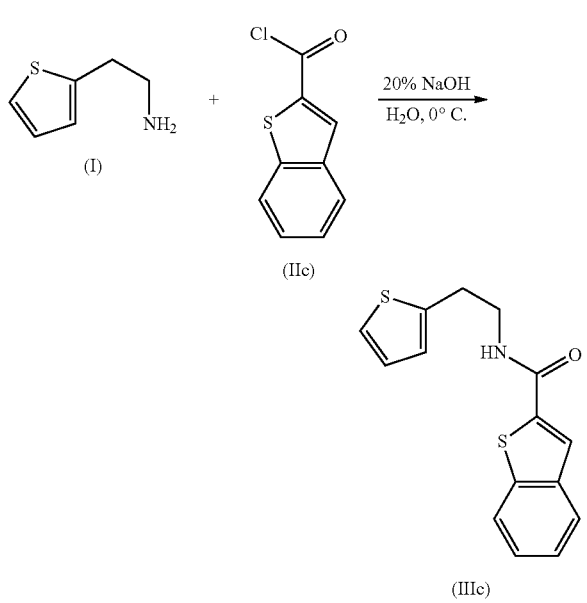

Compound (IIc) (benzo[b]thiophene-2-carbonyl chloride, 25 g, 127.13 mmol) and 150 mL of H$_2$O were added into a 500 mL single-neck bottle with an addition funnel. Next, compound (I) (2-(2-aminoethyl)thiophene, 19.4 g, 152.56 mmol, 1.2 eq.) was added dropwisely into the bottle via the addition funnel under ice-bath cooling. White solid was gradually formed. After dripping, a NaOH aqueous solution (20%) was added into the bottle and stirred overnight. After filtration with a porcelain funnel, a white solid of compound (IIIc) (35.2 g, yield of 96%) was obtained.

Step 2:

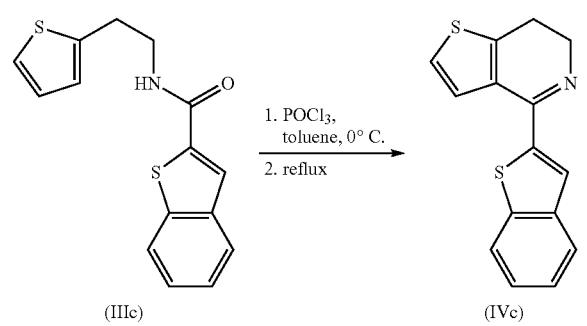 [SMILES: O=C(NCCc1cccs1)c1cc2ccccc2s1 ; c1ccc2sc(C3=NCCc4sccc43)cc2c1]

Compound (IIIc) (12 g, 41.81 mmol) and toluene (175 mL) were added into a 500 mL single-neck round-bottom flask. POCl$_3$ (12 mL, 125.43 mmol, 3 eq.) was added dropwisely into the flask via an addition funnel under ice-bath cooling. After dripping, the ice-bath was replaced by an oil bath and heated until toluene reflux. After reaction for two hours, a saturated NaHCO$_3$ aqueous solution was added into the flask for neutralization of the reaction. After toluene extraction, a toluene solution was collected and moisture was removed. After evaporation and standing for several hours, compound (IVc) (crystal, 9.8 g) was obtained with a yield of 79%.

Step 3:

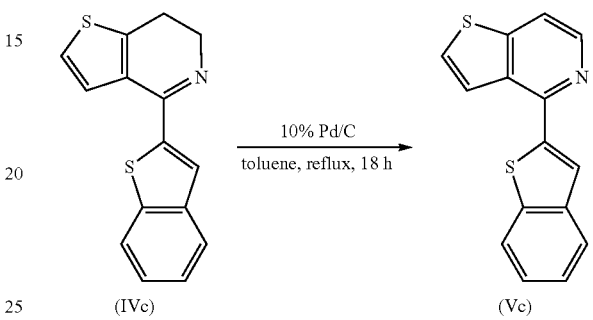

Compound (IVc) (9.8 g, 36.43 mmol), toluene (200 mL) and 10% Pd/C (15 g) were added into a 500 mL single-neck round-bottom flask and heated to toluene reflux. After reaction for 48 hours, the result was filtrated by diatomaceous earth (Celite 545) to remove Pd/C. After filtration, the filtrate was concentrated and purified by column chromatography (ethyl acetate/n-hexane=1/5), compound (Vc) (4.25 g) was obtained with a yield of 44%.

Step 4:

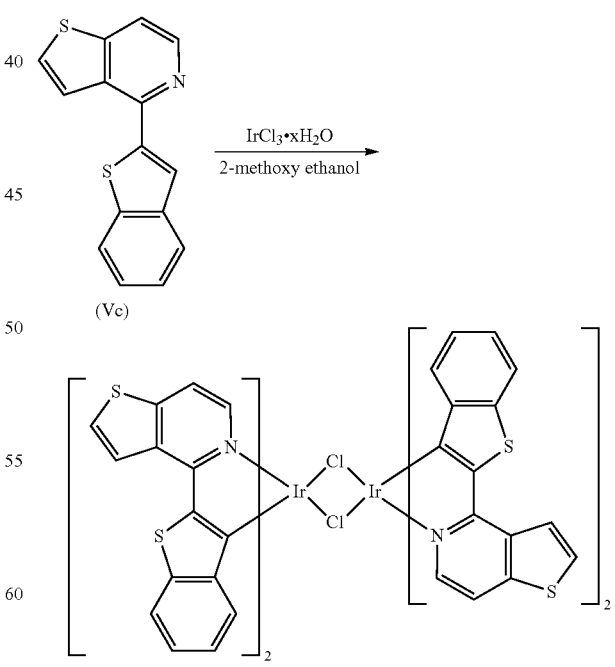

Compound (Vc) (5 g, 18.7 mmol, 2.2 eq.), IrCl$_3$xH$_2$O (2.54 g, 8.5 mmol), 2-methoxy ethanol (21 mL), and water (7 mL) were added into a 100 mL single-neck round-bottom flask. After heating to 140° C. and reacting for 24 hours, the reaction was quenched by adding plenty of water. After filtration, compound (VIc) (sepia solid, 7 g) was obtained with a yield of 54%.

Step 5:

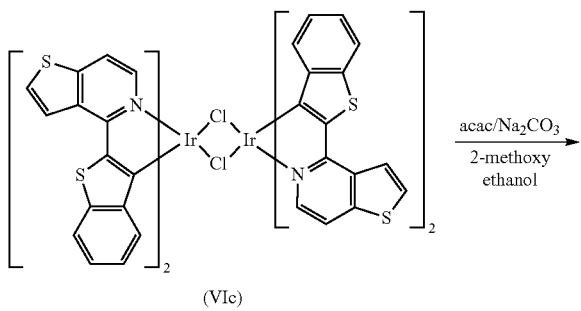

(VIc)

reacting for 24 hours and cooling to room temperature, the result was washed with 50 mL water and filtered to obtain orange solid product. The product was purified by column chromatography with dichloromethane/n-hexane (1/3), obtaining compound (PO-01-Bt-acac) (dark red solid product, 1.08 g) with a yield of 20%.

Compound (PO-01-Bt-acac) was analyzed by NMR spectroscopy. The spectral information of compound (PO-01-Bt-acac) is listed below:

$^1$H NMR (200 MHz, CDCl$_3$) δ 8.29 (d, J=6.2 Hz, 2H), 8.24 (d, J=5.6 Hz, 2H), 7.66-7.70 (m, 4H), 7.53 (d, J=5.8 Hz, 2H), 7.05 (t, J=7.4 Hz, 2H), 6.73 (d, J=8.2 Hz, 2H), 6.23 (d, J=8.0 Hz, 2H), 5.25 (s, 1H), 1.76 (s, 6H).

Example 4

Preparation of the Organic Metal Complex (PO-01-Np1-dipba, Ar=1-naphthyl)

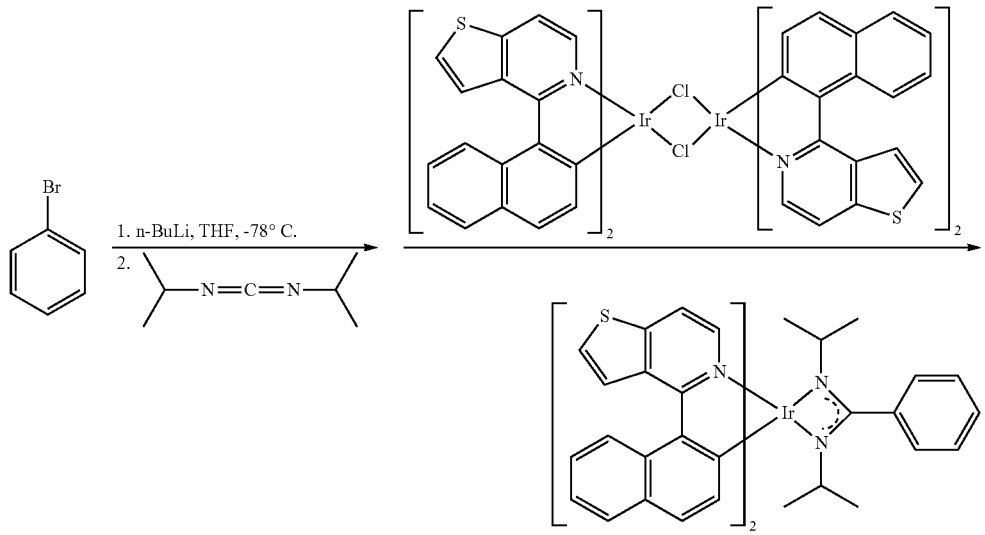

-continued

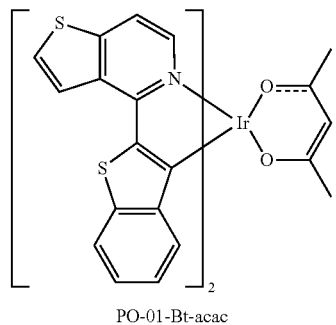

PO-01-Bt-acac

Compound (VIc) (5.0 g, 3.29 mmol), acetyl acetone (1.32 g, 13.16 mmol, 4 eq.), Na$_2$CO$_3$ (1.39 g, 13.16 mmol, 4 eq.), and 2-methoxyethanol (30 mL) were added into a 100 mL single-neck round-bottom flask and heated to 140° C. After Distilled THF (50 mL, anhydrous) and bromobenzene (1.46 mL, 13.91 mmol) were added into a 250 mL dual-neck round-bottom flask. After cooling to −78° C., n-BuLi (8.7 mL, 13.91 mmol) was added dropwisely into the flask. After dripping and stirring for 30 minutes, N,N-diisopropylcarbodiimide (2.2 mL, 13.91 mmol) was added dropwisely into the flask under −78° C. After dripping and rapid stirring for 30 minutes, a reaction mixture solution was obtained. The reaction mixture solution was then dripping into a THF solution (70 mL) containing compound (VIa) (5.2 g, 3.478 mmol) and heated to reflux. After reaction overnight, removal of solvent, filtration and washing with ether several times, compound (PO-01-Np1-dipba) (dark red solid product, 1.27 g) was obtained with a yield of 20%.

Compound (PO-01-Np1-dipba) was analyzed by NMR spectroscopy. The spectral information of compound (PO-01-Np1-dipba) is listed below:

$^1$H NMR (200 MHz, CDCl$_3$) δ 9.29 (d, J=6.8 Hz, 2H), 8.44 (d, J=4.0 Hz, 2H), 8.29 (d, J=5.6 Hz, 2H), 7.85 (d, J=4.8 Hz, 2H), 7.79 (d, J=5.6 Hz, 2H), 7.08-7.47 (m, 13H), 6.62 (s, 2H), 3.23 (m, 2H), 0.66 (d, J=6.2 Hz, 6H), −0.08 (d, J=6.2 Hz, 6H).

Example 5

Preparation of the Organic Metal Complex (PO-01-Np2-dipba, Ar=2-naphthyl)

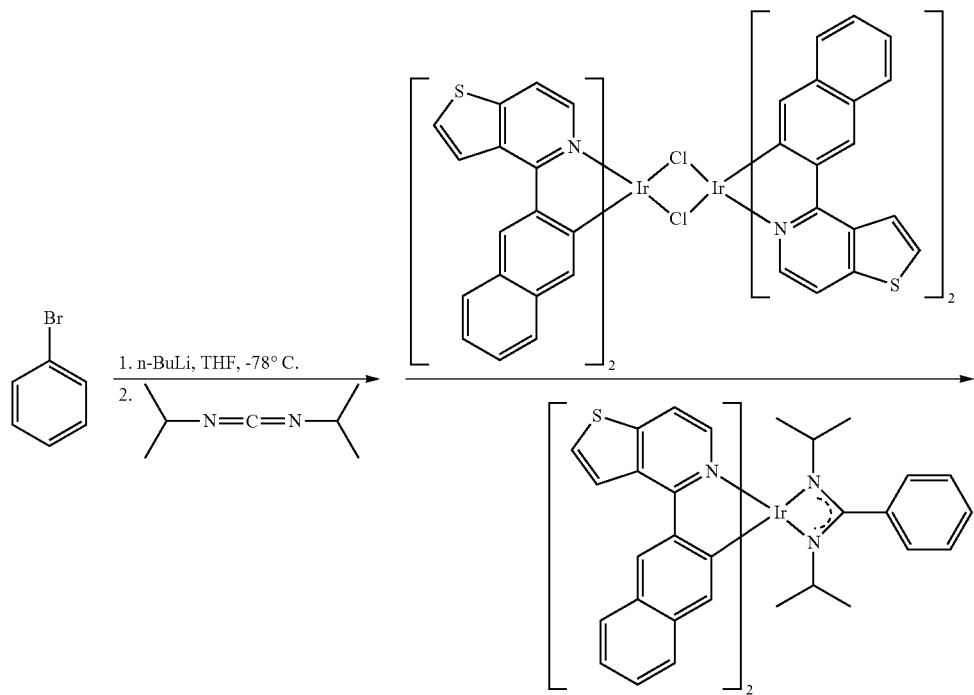

Distilled THF (50 mL, anhydrous) and bromobenzene (1.69 mL, 16.04 mmol) were added into a 250 mL dual-neck round-bottom flask. After cooling to −78° C., n-BuLi (10 mL, 16.04 mmol) was added dropwisely into the flask. After dripping and stirring for 30 minutes, N,N-diisopropylcarbodiimide (2.5 mL, 16.04 mmol) was added dropwisely into the flask under −78° C. After dripping and rapid stirring for 30 minutes, a reaction mixture solution was obtained. The reaction mixture solution was then dripping into a THF solution (70 mL) containing compound (VIb) (6 g, 4.01 mmol) and heated to reflux. After reaction overnight, removal of solvent, filtration and washing with ether several times, compound (PO-01-Np2-dipba) (dark red solid product, 3.13 g) was obtained with a yield of 39%.

Compound (PO-01-Np2-dipba) was analyzed by NMR spectroscopy. The spectral information of compound (PO-01-Np2-dipba) is listed below:

$^1$H NMR (200 MHz, CDCl$_3$) δ 9.59 (d, J=6.8 Hz, 2H), 8.64 (d, J=4.0 Hz, 2H), 8.59 (d, J=5.6 Hz, 2H), 7.85 (d, J=4.8 Hz, 2H), 7.79 (d, J=5.6 Hz, 2H), 7.09-7.42 (m, 13H), 6.67 (s, 2H), 3.24 (m, 2H), 0.70 (d, J=6.2 Hz, 6H), −0.10 (d, J=6.2 Hz, 6H).

Example 6

Preparation of the Organic Metal Complex (PO-01-Bt-dipba, Ar=benzothienyl)

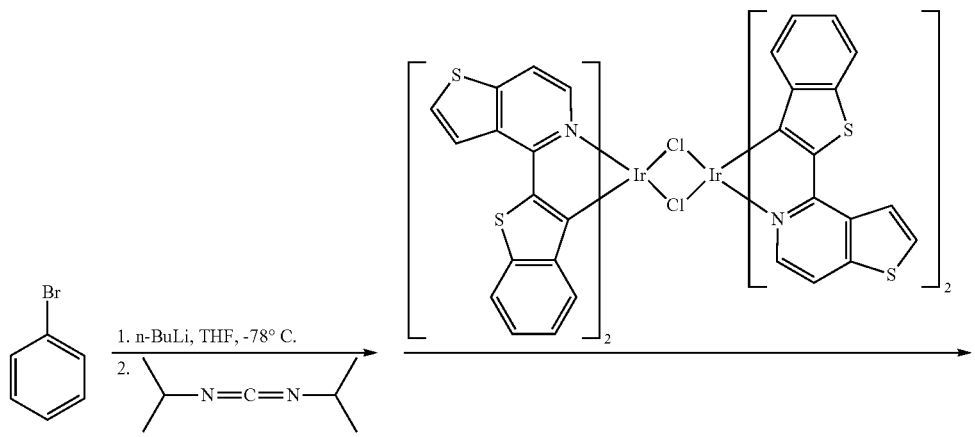

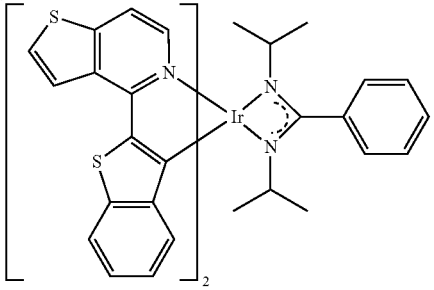

Distilled THF (50 mL, anhydrous) and bromobenzene (1.9 mL, 18.44 mmol) were added into a 250 mL dual-neck round-bottom flask. After cooling to −78° C., n-BuLi (11.5 mL, 18.44 mmol) was added dropwisely into the flask. After dripping and stirring for 30 minutes, N,N-diisopropylcarbodiimide (2.87 mL, 18.44 mmol) was added dropwisely into the flask under −78° C. After dripping and rapid stirring for 30 minutes, a reaction mixture solution was obtained. The reaction mixture solution was then dripping into a THF solution (70 mL) containing compound (VIc) (7 g, 4.61 mmol) and heated to reflux. After reaction overnight, removal of solvent, filtration and washing with ether several times, compound (PO-01-Bt-dipba) (dark red solid product, 5.82 g) was obtained with a yield of 65%.

Compound (PO-01-Bt-dipba) was analyzed by NMR spectroscopy. The spectral information of compound (PO-01-Bt-dipba) is listed below:

$^1$H NMR (200 MHz, CDCl$_3$) δ 9.37 (d, J=6.6 Hz, 2H), 8.25 (d, J=4.8 Hz, 2H), 7.66-7.74 (m, 6H), 7.42 (d, J=7.6 Hz, 4H), 7.29 (d, J=2.2 Hz, 1H), 7.05 (t, J=6.8 Hz, 2H), 6.73 (t, J=7.4 Hz, 2H), 6.33 (d, J=8.2 Hz, 2H), 3.18 (m, 2H), 0.55 (d, J=6.2 Hz, 6H), −0.14 (d, J=6.8 Hz, 6H).

Example 7

Preparation of the Organic Metal Complex (PO-01-Np1-dipig, Ar=1-naphthyl)

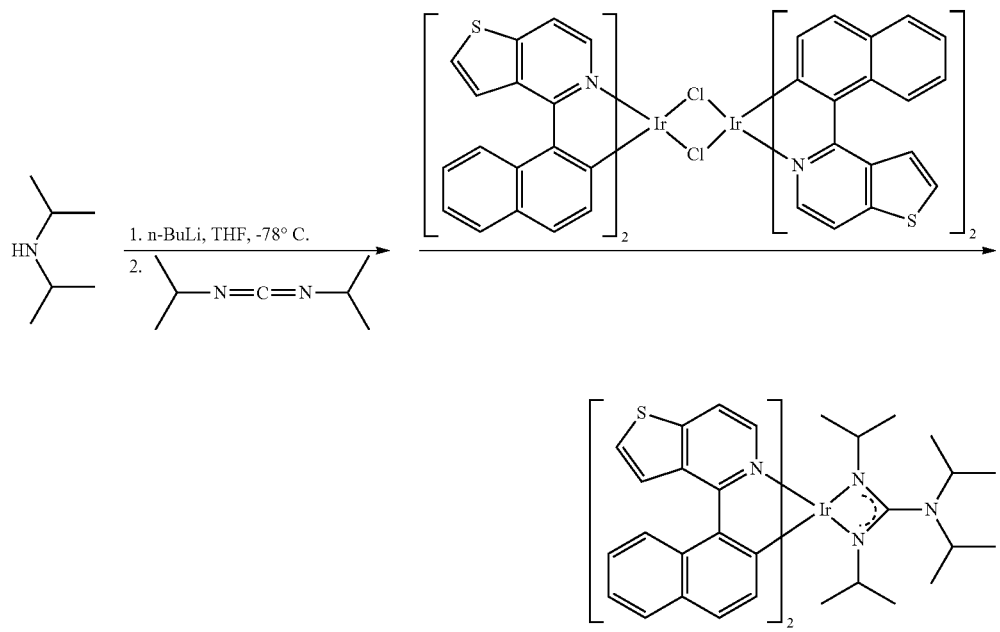

Distilled THF (50 mL, anhydrous) and diisopropylamine (2 mL, 13.91 mmol) were added into a 250 mL dual-neck round-bottom flask. After cooling to −78° C., n-BuLi (8.7 mL, 8.96 mmol) was added dropwisely into the flask. After dripping and stirring for 30 minutes, N,N-diisopropylcarbodiimide (2.17 mL, 13.91 mmol) was added dropwisely into the flask under −78° C. After dripping and rapid stirring for 30 minutes, a reaction mixture solution was obtained. The reaction mixture solution was then dripping into a THF solution (50 mL) containing compound (VIa) (5.2 g, 3.478 mmol) and heated to reflux. After reaction overnight, removal of solvent, filtration and washing with ether several times, compound (PO-01-Np1-dipig) (dark red solid product, 1.41 g) was obtained with a yield of 25%.

Compound (PO-01-Np1-dipig) was analyzed by NMR spectroscopy. The spectral information of compound (PO-01-Np1-dipig) is listed below:

$^1$H NMR (200 MHz, CDCl$_3$) δ 9.18 (d, J=6.6 Hz, 2H), 8.55 (s, 2H), 8.45 (d, J=5.4 Hz, 2H), 7.56-7.77 (m, 5H), 6.50-7.16 (m, 7H), 6.62 (s, 2H), 3.80 (m, 2H), 3.48 (m, 2H), 1.14-1.30 (m, 12H), 0.82 (d, J=7.2 Hz, 6H), −0.08 (d, J=6.0 Hz, 6H).

Example 8

Preparation of the Organic Metal Complex
(PO-01-Np2-dipig, Ar=2-naphthyl)

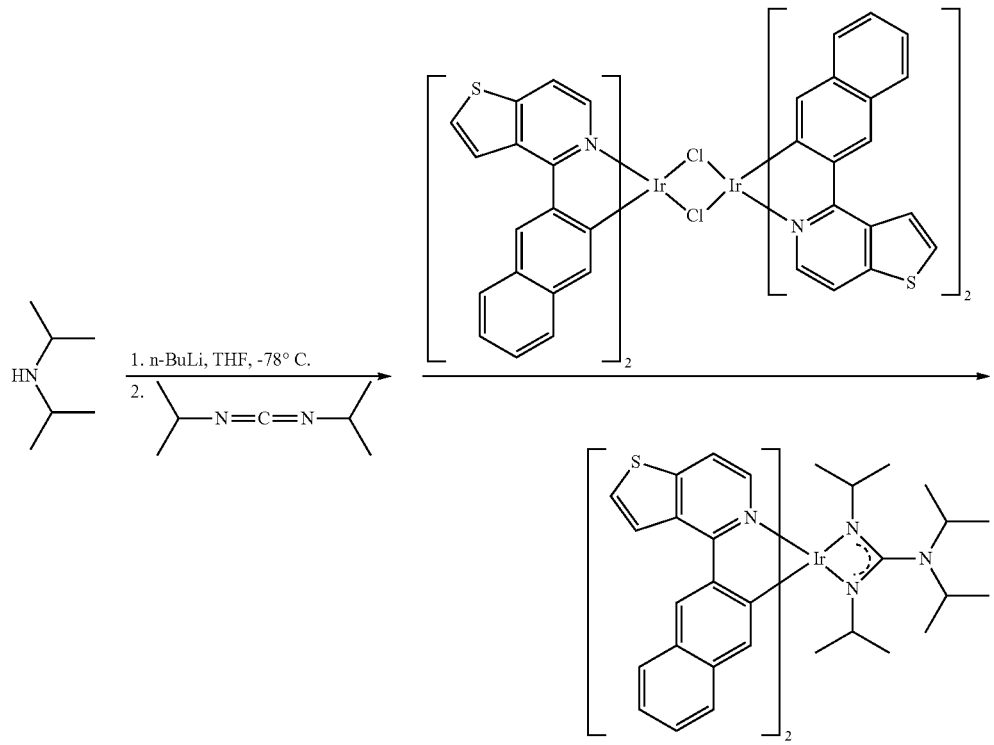

Distilled THF (30 mL, anhydrous) and diisopropylamine (2.7 mL, 16.04 mmol) were added into a 250 mL dual-neck round-bottom flask. After cooling to −78° C., n-BuLi (10 mL, 16.04 mmol) was added dropwisely into the flask. After dripping and stirring for 30 minutes, N,N-diisopropylcarbodiimide (2.5 mL, 16.04 mmol) was added dropwisely into the flask under −78° C. After dripping and rapid stirring for 30 minutes, a reaction mixture solution was obtained. The reaction mixture solution was then dripping into a THF solution (70 mL) containing compound (VIb) (6 g, 4.01 mmol) and heated to reflux. After reaction overnight, removal of solvent, filtration and washing with ether several times, compound (PO-01-Np2-dipig) (dark red solid product, 1.43 g) was obtained with a yield of 22%.

Compound (PO-01-Np2-dipig) was analyzed by NMR spectroscopy. The spectral information of compound (PO-01-Np2-dipig) is listed below:

$^1$H NMR (200 MHz, CDCl$_3$) δ 9.36 (d, J=6.6 Hz, 2H), 8.63 (s, 2H), 8.55 (d, J=5.4 Hz, 2H), 7.65-7.79 (m, 5H), 6.59-7.16 (m, 7H), 6.60 (s, 2H), 3.82 (m, 2H), 3.55 (m, 2H), 1.14-1.30 (m, 12H), 0.84 (d, J=7.2 Hz, 6H), −0.06 (d, J=6.0 Hz, 6H).

Example 9

Preparation of the Organic Metal Complex
(PO-01-Bt-dipig, Ar=benzothienyl)

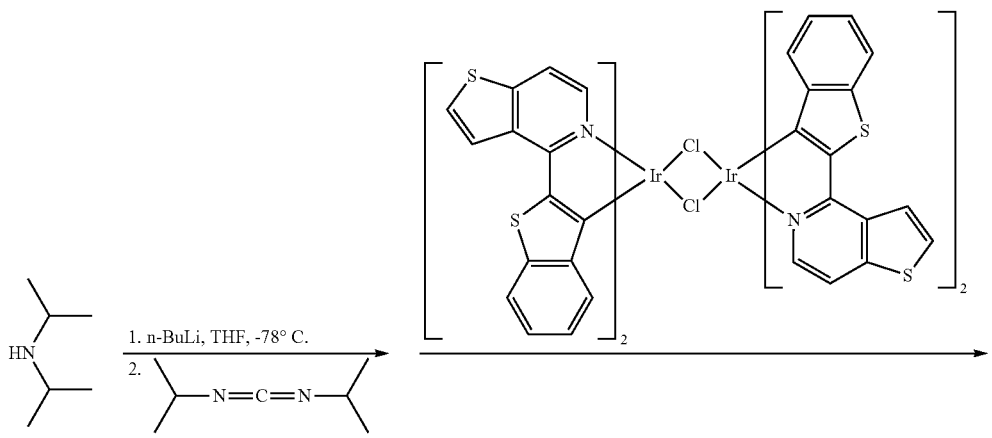

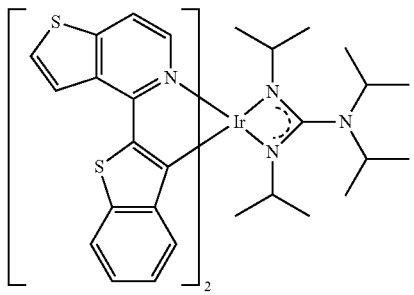

Distilled THF (50 mL, anhydrous) and diisopropylamine (2.6 mL, 18.44 mmol) were added into a 250 mL dual-neck round-bottom flask. After cooling to −78° C., n-BuLi (11.5 mL, 18.44 mmol) was added dropwisely into the flask. After dripping and stirring for 30 minutes, N,N-diisopropylcarbodiimide (2.87 mL, 18.44 mmol) was added dropwisely into the flask under −78° C. After dripping and rapid stirring for 30 minutes, a reaction mixture solution was obtained. The reaction mixture solution was then dripping into a THF solution (70 mL) containing compound (VIc) (7 g, 4.61 mmol) and heated to reflux. After reaction overnight, removal of solvent, filtration and washing with ether several times, compound (PO-01-Bt-dipig) (dark red solid product, 2.28 g) was obtained with a yield of 30%.

Compound (PO-01-Bt-dipig) was analyzed by NMR spectroscopy. The spectral information of compound (PO-01-Bt-dipig) is listed below:

$^1$H NMR (200 MHz, CDCl$_3$) δ 9.18 (d, J=6.6 Hz, 2H), 8.20 (d, J=5.4 Hz, 2H), 7.56-7.71 (m, 6H), 7.04 (t, J=6.0 Hz, 2H), 6.70 (t, J=6.0, 2H), 6.20 (d, J=8.1 Hz), 3.65-3.81 (m, 2H), 3.51 (q, 2H), 1.19-1.61 (m, 12H), 0.76 (d, J=5.0 Hz, 6H), −0.10 (d, J=6.4 Hz, 6H).

Example 10

Preparation of the Organic Metal Complex (PO-01-TB-dipig, Ar=4-tBu-benzyl)

Step 1:

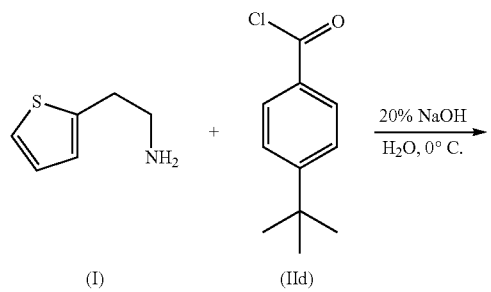

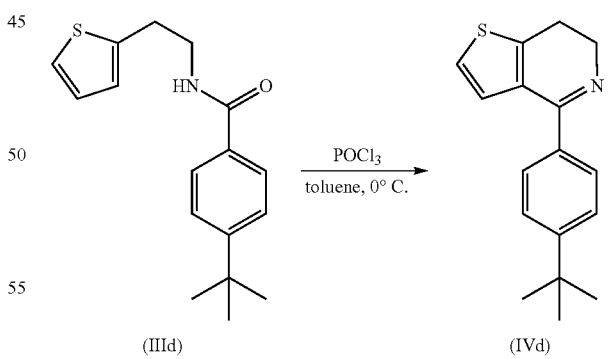

Compound (I) (2-(2-aminoethyl)thiophene, 34.89 g, 274.8 mmol, 1.2 eq.) and 200 mL H$_2$O were added into a 500 mL single-neck bottle with an addition funnel. Next, Compound (IId) (4-tert-butylbenzoyl chloride, 45 g, 229 mmol) was added dropwisely into the bottle via the addition funnel under ice-bath cooling. White solid was gradually formed. After dripping, a NaOH aqueous solution (20%) was added into the bottle and stirred overnight. After filtration with a porcelain funnel, a white solid of compound (IIId) (63 g, yield of 95%) was obtained.

Step 2:

Compound (IIId) (12 g, 41.81 mmol) and toluene (175 mL) were added into a 250 mL single-neck round-bottom flask. POCl$_3$ (11.7 mL, 125.43 mmol, 3 eq.) was added dropwisely into the flask via an addition funnel under ice-bath cooling. After dripping, the ice-bath was replaced by an oil bath and heated until toluene reflux. After reaction for two hours, a saturated NaHCO$_3$ aqueous solution was added into the flask for neutralization of the reaction. After toluene extraction, a toluene solution was collected and moisture was removed. After evaporation and standing for several hours, compound (IVd) (crystal, 11 g) was obtained with a yield of 98%.

Step 3:

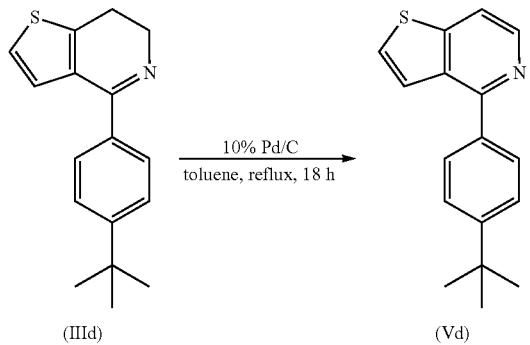 [SMILES: CC(C)(C)c1ccc(C2=NCCc3sccc32)cc1 ; "10% Pd/C" ; CC(C)(C)c1ccc(-c2nccc3sccc23)cc1]

Compound (IVd) (11 g, 40.89 mmol), toluene (100 mL) and 10% Pd/C (10 g) were added into a 250 mL single-neck round-bottom flask and heated to toluene reflux. After reaction for 48 hours, the result was filtrated by diatomaceous earth (Celite 545) to remove Pd/C. After filtration, the filtrate was concentrated and purified by column chromatography (ethyl acetate/n-hexane=1/5), compound (Vd) (10 g) was obtained with a yield of 92%.

Step 4:

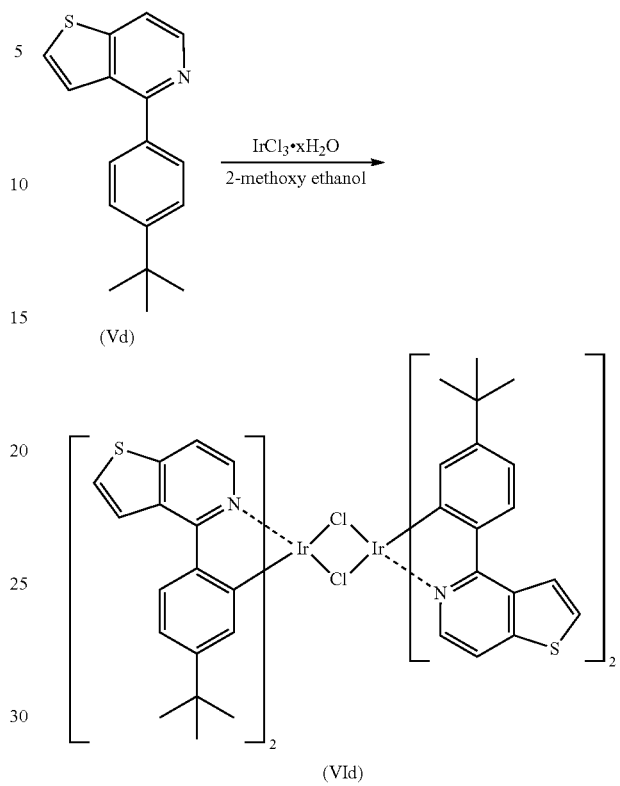

Compound (Vd) (5 g, 18.7 mmol, 2.2 eq.), IrCl₃·xH₂O (2.5 g, 8.5 mmol), 2-methoxy ethanol (15 mL), and water (5 mL) were added into a 100 mL single-neck round-bottom flask. After heating to 140° C. and reacting for 24 hours, the reaction was quenched by adding plenty of water. After filtration, compound (VId) (orange solid, 5.5 g) was obtained with a yield of 44%.

Step 5:

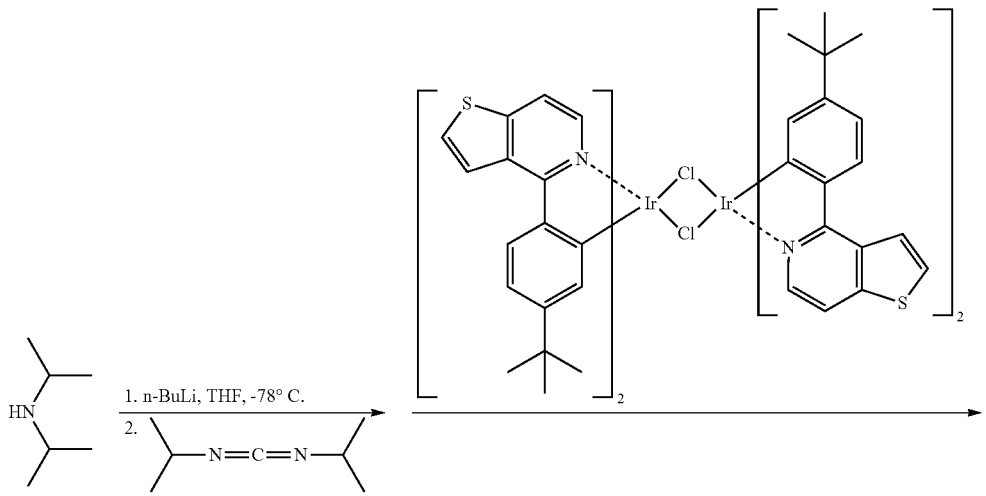

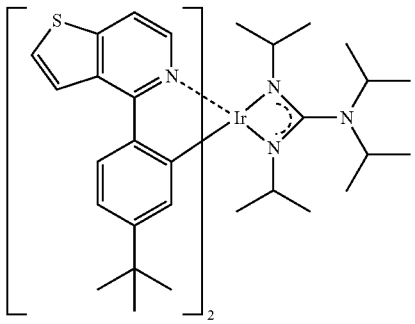

Distilled THF (50 mL, anhydrous) and diisopropylamine (2.1 mL, 14.48 mmol) were added into a 250 mL dual-neck round-bottom flask. After cooling to −78° C., n-BuLi (9.1 mL, 14.48 mmol) was added dropwisely into the flask. After dripping and stirring for 30 minutes, N,N-diisopropylcarbodiimide (2.3 mL, 8.96 mmol) was added dropwisely into the flask under −78° C. After dripping and rapid stirring for 30 minutes, a reaction mixture solution was obtained. The reaction mixture solution was then dripping into a THF solution (70 mL) containing compound (VId) (5.5 g, 3.62 mmol) and heated to reflux. After reaction overnight, removal of solvent, filtration and washing with ether several times, compound (PO-01-TB-dipig) (dark red solid product, 3.01 g) was obtained with a yield of 51%.

Compound (PO-01-TB-dipig) was analyzed by NMR spectroscopy. The spectral information of compound (PO-01-TB-dipig) is listed below:

$^1$H NMR (200 MHz, CDCl$_3$) δ 9.21 (d, J=6.6 Hz, 2H), 8.24 (d, J=5.8 Hz, 2H), 7.94 (d, J=8.4 Hz, 2H), 7.57-7.65 (m, 4H), 6.81 (dd, J=8.0, 2.2 Hz, 2H), 6.22 (s, 2H), 3.79 (m, 2H), 3.51 (m, 2H), 1.22 (m, 12H), 0.92 (s, 18H), 0.82 (d, J=6.2 Hz, 6H), −0.05 (d, J=6.2 Hz, 6H).

Organic Electroluminescent Devices

Example 11

Preparation of the Organic Electroluminescent Device (1) (Through Dry Process)

A glass substrate with a patterned indium tin oxide (ITO) film of 150 nm was provided and then washed with a neutral cleaning agent, acetone, and ethanol with ultrasonic agitation. After drying the substrate with a nitrogen flow, the substrate was subjected to a UV/ozone treatment for 30 minutes. Next, PEDOT (poly(3,4)-ethylendioxythiophen) and PSS (e-polystyrenesulfonate) were selected to coat on the ITO film by a spin coating process (with a rotation rate of 2,000 rpm) to form a PEDOT:PSS film (with a thickness of 45 nm, serving as a hole injection layer). After heating to 130° C. for 10 min, a TAPC (di-[4-(N,N-ditolyl-amino)-phenyl]cyclohexane) layer (with a thickness of 35 nm), a TCTA (4,4',4''-tris(carbazol-9-yl)triphenylamine) layer doped with compound (PO-01-Np2-acac)

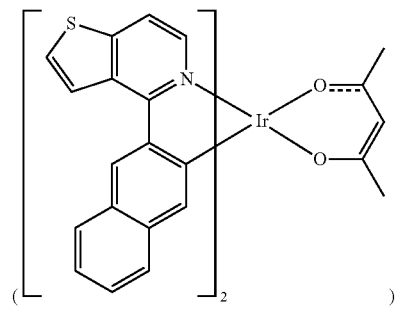

(the ratio between TCTA and compound (PO-01-Np2-acac) was 100:6, with a thickness of 10 nm), a TmPyPB (1,3,5-tri[(3-pyridyl)-phen-3-yl]benzene) layer (with a thickness of 42 nm), a LiF layer (with a thickness of 0.5 nm), and an Al layer (with a thickness of 120 nm) were subsequently deposited on the ITO film under 10$^{-6}$ torr and packaged, obtaining the organic electroluminescent device (1). The structure of the organic electroluminescent device (1) is described in the following:

ITO (150 nm)/PEDOT:PSS (45 nm)/TAPC (35 nm)/TCTA: compound (PO-01-Np2-acac) (6%, 10 nm)/TmPyPB (42 nm)/LiF (0.5 nm)/Al (120 nm)

The optical properties including brightness (cd/m$^2$), current efficiency (cd/A), power efficiency (lm/W), emission wavelength (nm), and color coordinates (x, y) of the organic electroluminescent device (1) were measured and the results are described in Table 2.

Example 12

Preparation of the Organic Electroluminescent Device (2) (Through Dry Process)

The preparation of the organic electroluminescent device (2) of this example is similar to that of Example 11. The distinction therebetween is that the compound-doping TCTA layer was prepared by doping compound (PO-01-Np2-dipba) into TCTA. The structure of the organic electroluminescent device (2) is described in the following:

ITO (150 nm)/PEDOT:PSS (45 nm)/TAPC (35 nm)/TCTA: compound (PO-01-Np2-dipba) (6%, 10 nm)/TmPyPB (42 nm)/LiF (0.5 nm)/Al (120 nm)

The optical properties including brightness (cd/m$^2$), current efficiency (cd/A), power efficiency (lm/W), emission wavelength (nm), and color coordinates (x, y) of the organic electroluminescent device (2) were measured and the results are described in Table 2.

Example 13

Preparation of the Organic Electroluminescent Device (3) (Through Dry Process)

The preparation of the organic electroluminescent device (3) of this example is similar to that of Example 11. The distinction therebetween is that the compound-doping TCTA layer was prepared by doping compound (PO-01-Np2-dipig) into TCTA. The structure of the organic electroluminescent device (3) is described in the following:

ITO (150 nm)/PEDOT:PSS (45 nm)/TAPC (35 nm)/TCTA: compound (PO-01-Np2-dipig) (6%, 10 nm)/TmPyPB (42 nm)/LiF (0.5 nm)/Al (120 nm)

The optical properties including brightness (cd/m²), current efficiency (cd/A), power efficiency (lm/W), emission wavelength (nm), and color coordinates (x, y) of the organic electroluminescent device (3) were measured and the results are described in Table 2.

Example 14

Preparation of the Organic Electroluminescent Device (4) (Through Wet Process)

A glass substrate with a patterned indium tin oxide (ITO) film of 150 nm was provided and then washed with a neutral cleaning agent, acetone, and ethanol with ultrasonic agitation. After drying the substrate with a nitrogen flow, the substrate was subjected to a UV/ozone treatment for 30 minutes. Next, PEDOT (poly(3,4)-ethylendioxythiophen) and PSS (e-polystyrenesulfonate) were selected to coat on the ITO film by a spin coating process (with a rotation rate of 2,000 rpm) to form a PEDOT:PSS film (with a thickness of 45 nm, serving as a hole injection layer). After heating to 130° C. for 10 min, a light-emitting film (with a thickness of 30 nm) was formed on the PEDOT:PSS film by a spin coating process. The composition of the light-emitting film included TCTA (4,4',4"-tris(carbazol-9-yl)triphenylamine) and compound (PO-01-Np2-acac)

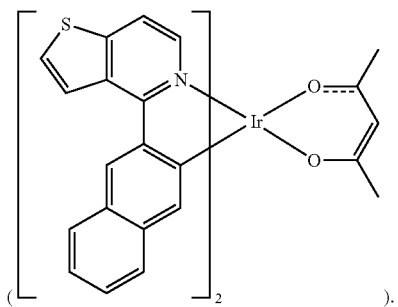

TCTA and compound (PO-01-Np2-acac) (the weight ratio between TCTA and compound (PO-01-Np2-acac) was 94:6) were dissolved in chlorobenzene to prepare the light-emitting film. Next, a TmPyPB (1,3,5-tri[(3-pyridyl)-phen-3-yl] benzene) layer (with a thickness of 50 nm, serving as a hole-block/electron-transport layer) was deposited on the light-emitting film. Next, a LiF layer (with a thickness of 1 nm) and an Al layer (with a thickness of 100 nm) were subsequently deposited on the TmPyPB film and packaged, obtaining the organic electroluminescent device (4). The structure of the organic electroluminescent device (4) is described in the following:

ITO (150 nm)/PEDOT:PSS (45 nm)/TCTA: compound (PO-01-Np2-acac) (30 nm)/TmPyPB (50 nm)/LiF (1 nm)/Al (100 nm)

The optical properties including brightness (cd/m²), current efficiency (cd/A), power efficiency (lm/W), emission wavelength (nm), and color coordinates (x, y) of the organic electroluminescent device (4) were measured and the results are described in Table 2.

Example 15

Preparation of the Organic Electroluminescent Device (5) (Through Wet Process)

The preparation of the organic electroluminescent device (5) of this example is similar to that of Example 14. The distinction therebetween is that the composition of the light-emitting film included NPB and compound (PO-01-Np2-dipba). The structure of the organic electroluminescent device (5) is described in the following:

ITO (150 nm)/PEDOT:PSS (45 nm)/NPB: compound (PO-01-Np2-dipba) (30 nm)/TmPyPB (55 nm)/LiF (1 nm)/Al (100 nm)

The optical properties including brightness (cd/m²), current efficiency (cd/A), power efficiency (lm/W), emission wavelength (nm), and color coordinates (x, y) of the organic electroluminescent device (5) were measured and the results are described in Table 2.

Example 16

Preparation of the Organic Electroluminescent Device (6) (Through Wet Process)

The preparation of the organic electroluminescent device (6) of this example is similar to that of Example 14. The distinction therebetween is that the composition of the light-emitting film included NPB and compound (PO-01-Np2-dipig). The structure of the organic electroluminescent device (6) is described in the following:

ITO (150 nm)/PEDOT:PSS (45 nm)/NPB: compound (PO-01-Np2-dipig) (30 nm)/TmPyPB (55 nm)/LiF (1 nm)/Al (100 nm)

The optical properties including brightness (cd/m²), current efficiency (cd/A), power efficiency (lm/W), emission wavelength (nm), and color coordinates (x, y) of the organic electroluminescent device (6) were measured and the results are described in Table 2.

Example 17

Preparation of the Organic Electroluminescent Device (7) (Through Dry Process)

The preparation of the organic electroluminescent device (7) of this example is similar to that of Example 11. The distinction therebetween is that the compound-doping TCTA layer was prepared by doping compound (PO-01-Bt-acac) into TCTA. The structure of the organic electroluminescent device (7) is described in the following:

ITO (150 nm)/PEDOT:PSS (45 nm)/TAPC (35 nm)/TCTA: compound (PO-01-Bt-acac) (6%, 10 nm)/TmPyPB (42 nm)/LiF (0.5 nm)/Al (120 nm)

The optical properties including brightness (cd/m²), current efficiency (cd/A), power efficiency (lm/W), emission wavelength (nm), and color coordinates (x, y) of the organic electroluminescent device (7) were measured and the results are described in Table 2.

Example 18

Preparation of the Organic Electroluminescent Device (8) (Through Dry Process)

The preparation of the organic electroluminescent device (8) of this example is similar to that of Example 11. The distinction therebetween is that the compound-doping TCTA layer was prepared by doping compound (PO-01-Bt-dipba) into TCTA. The structure of the organic electroluminescent device (8) is described in the following:

ITO (150 nm)/PEDOT:PSS (45 nm)/TAPC (35 nm)/ TCTA: compound (PO-01-Bt-dipba) (6%, 10 nm)/TmPyPB (42 nm)/LiF (0.5 nm)/Al (120 nm)

The optical properties including brightness ($cd/m^2$), current efficiency (cd/A), power efficiency (lm/W), emission wavelength (nm), and color coordinates (x, y) of the organic electroluminescent device (8) were measured and the results are described in Table 2.

Example 19

Preparation of the Organic Electroluminescent Device (9) (Through Dry Process)

The preparation of the organic electroluminescent device (9) of this example is similar to that of Example 11. The distinction therebetween is that the compound-doping TCTA layer was prepared by doping compound (PO-01-Bt-dipig) into TCTA. The structure of the organic electroluminescent device (9) is described in the following:

ITO (150 nm)/PEDOT:PSS (45 nm)/TAPC (35 nm)/ TCTA: compound (PO-01-Bt-dipig) (6%, 10 nm)/TmPyPB (42 nm)/LiF (0.5 nm)/Al (120 nm)

The optical properties including brightness ($cd/m^2$), current efficiency (cd/A), power efficiency (lm/W), emission wavelength (nm), and color coordinates (x, y) of the organic electroluminescent device (9) were measured and the results are described in Table 2.

Example 20

Preparation of the Organic Electroluminescent Device (10) (Through Wet Process)

The preparation of the organic electroluminescent device (10) of this example is similar to that of Example 14. The distinction therebetween is that the composition of the light-emitting film included NPB and compound (PO-01-Bt-acac). The structure of the organic electroluminescent device (10) is described in the following:

ITO (150 nm)/PEDOT:PSS (45 nm)/NPB: compound (PO-01-Bt-acac) (30 nm)/TmPyPB (55 nm)/LiF (1 nm)/Al (100 nm)

The optical properties including brightness ($cd/m^2$), current efficiency (cd/A), power efficiency (lm/W), emission wavelength (nm), and color coordinates (x, y) of the organic electroluminescent device (10) were measured and the results are described in Table 2.

Example 21

Preparation of the Organic Electroluminescent Device (11) (Through Wet Process)

The preparation of the organic electroluminescent device (11) of this example is similar to that of Example 14. The distinction therebetween is that the composition of the light-emitting film included NPB and compound (PO-01-Bt-dipba). The structure of the organic electroluminescent device (11) is described in the following:

ITO (150 nm)/PEDOT:PSS (45 nm)/NPB: compound (PO-01-Bt-dipba) (30 nm)/TmPyPB (55 nm)/LiF (1 nm)/Al (100 nm)

The optical properties including brightness ($cd/m^2$), current efficiency (cd/A), power efficiency (lm/W), emission wavelength (nm), and color coordinates (x, y) of the organic electroluminescent device (11) were measured and the results are described in Table 2.

Example 22

Preparation of the Organic Electroluminescent Device (12) (Through Wet Process)

The preparation of the organic electroluminescent device (12) of this example is similar to that of Example 14. The distinction therebetween is that the composition of the light-emitting film included NPB and compound (PO-01-Bt-dipig). The structure of the organic electroluminescent device (12) is described in the following:

ITO (150 nm)/PEDOT:PSS (45 nm)/NPB: compound (PO-01-Bt-dipig) (30 nm)/TmPyPB (55 nm)/LiF (1 nm)/Al (100 nm)

The optical properties including brightness ($cd/m^2$), current efficiency (cd/A), power efficiency (lm/W), emission wavelength (nm), and color coordinates (x, y) of the organic electroluminescent device (12) were measured and the results are described in Table 2.

Example 23

Preparation of the Organic Electroluminescent Device (13) (Through Dry Process)

The preparation of the organic electroluminescent device (13) of this example is similar to that of Example 11. The distinction therebetween is that the compound-doping TCTA layer was prepared by doping compound (PO-01-TB-dipig) into TCTA. The structure of the organic electroluminescent device (13) is described in the following:

ITO (150 nm)/PEDOT:PSS (45 nm)/TAPC (35 nm)/ TCTA: compound (PO-01-TB-dipig) (6%, 10 nm)/TmPyPB (42 nm)/LiF (0.5 nm)/Al (120 nm)

The optical properties including brightness ($cd/m^2$), current efficiency (cd/A), power efficiency (lm/W), emission wavelength (nm), and color coordinates (x, y) of the organic electroluminescent device (13) were measured and the results are described in Table 2.

Example 24

Preparation of the Organic Electroluminescent Device (14) (Through Wet Process)

The preparation of the organic electroluminescent device (14) of this example is similar to that of Example 14. The distinction therebetween is that the composition of the light-emitting film included NPB and compound (PO-01-TB-dipig). The structure of the organic electroluminescent device (14) is described in the following:

ITO (150 nm)/PEDOT:PSS (45 nm)/NPB: compound (PO-01-TB-dipig) (30 nm)/TmPyPB (55 nm)/LiF (1 nm)/Al (100 nm)

The optical properties including brightness (cd/m$^2$), current efficiency (cd/A), power efficiency (lm/W), emission wavelength (nm), and color coordinates (x, y) of the organic electroluminescent device (14) were measured and the results are described in Table 2.

Comparative Example 1

Preparation of a Conventional Organic Electroluminescent Device (Through Dry Process)

The preparation of the organic electroluminescent device of this comparative example is similar to that of Example 11. The distinction therebetween is that the compound-doping TCTA layer was prepared by doping compound (Ir(phq)$_2$acac) into TCTA. The structure of the conventional organic electroluminescent device is described in the following:

ITO (150 nm)/PEDOT:PSS (45 nm)/TAPC (35 nm)/TCTA: compound (Ir(phq)$_2$acac) (6%, 10 nm)/TmPyPB (42 nm)/LiF (0.5 nm)/Al (120 nm)

The optical properties including brightness (cd/m$^2$), current efficiency (cd/A), power efficiency (lm/W), emission wavelength (nm), and color coordinates (x, y) of the conventional organic electroluminescent device were measured and the results are described in Table 2.

Comparative Example 2

Preparation of a Conventional Organic Electroluminescent Device (Through Wet Process)

The preparation of the organic electroluminescent device of this comparative example is similar to that of Example 14. The distinction therebetween is that the composition of the light-emitting film included TCTA and compound (Ir(phq)$_2$acac). The structure of the conventional organic electroluminescent device is described in the following:

ITO (150 nm)/PEDOT:PSS (45 nm)/TCTA: compound (Ir(phq)$_2$acac) (30 nm)/TmPyPB (45 nm)/LiF (1 nm)/Al (100 nm)

The optical properties including brightness (cd/m$^2$), current efficiency (cd/A), power efficiency (lm/W), emission wavelength (nm), and color coordinates (x, y) of the conventional organic electroluminescent device were measured and the results are described in Table 2.

TABLE 2

| Examples/Com. Examples | Organic metal complexes | Voltage (V) | Brightness (cd/m$^2$) | Current efficiency (cd/A) | Power efficiency (lm/W) | Emission wavelength (nm) | CIE (x, y) |
|---|---|---|---|---|---|---|---|
| Example 11 Organic electroluminescent device (1) | PO-01-Np2-acac | 4.4 | 1000 | 25.7 | 22.4 | 604 | (0.60, 0.40) |
| Example 12 Organic electroluminescent device (2) | PO-01-Np2-dipba | 7.3 | 1000 | 15.2 | 6.6 | 612 | (0.64, 0.35) |
| Example 13 Organic electroluminescent device (3) | PO-01-Np2-dipig | 5.0 | 1000 | 11.2 | 7.0 | 624 | (0.67, 0.33) |
| Example 14 Organic electroluminescent device (4) | PO-01-Np2-acac | 4.4 | 1000 | 22.5 | 16.1 | 596 | (0.56, 0.44) |
| Example 15 Organic electroluminescent device (5) | PO-01-Np2-dipba | 4.9 | 1000 | 10.5 | 6.8 | 612 | (0.63, 0.36) |
| Example 16 Organic electroluminescent device (6) | PO-01-Np2-dipig | 4.6 | 1000 | 9.4 | 6.4 | 624 | (0.67, 0.33) |
| Example 17 Organic electroluminescent device (7) | PO-01-Bt-acac | 5.0 | 580 | 6.8 | 4.3 | 650 | (0.68, 0.32) |
| Example 18 Organic electroluminescent device (8) | PO-01-Bt-dipba | 14.0 | 959 | 0.25 | 0.06 | 664 | (0.68, 0.28) |
| Example 19 Organic electroluminescent device (9) | PO-01-Bt-dipig | 6.0 | 1000 | 2.8 | 1.5 | 660 | (0.68, 0.27) |
| Example 20 Organic electroluminescent device (10) | PO-01-Bt-acac | 8.0 | 470 | 3.8 | 1.5 | 654 | (0.68, 0.32) |

TABLE 2-continued

| Examples/ Com. Examples | Organic metal complexes | Voltage (V) | Brightness (cd/m$^2$) | Current efficiency (cd/A) | Power efficiency (lm/W) | Emission wavelength (nm) | CIE (x, y) |
|---|---|---|---|---|---|---|---|
| Example 21 Organic electroluminescent device (11) | PO-01-Bt-dipba | 7.5 | 314 | 0.4 | 0.2 | 660 | (0.68, 0.27) |
| Example 22 Organic electroluminescent device (12) | PO-01-Bt-dipig | 7.0 | 957 | 3.6 | 1.6 | 658 | (0.68, 0.32) |
| Example 23 Organic electroluminescent device (13) | PO-01-TB-dipig | 4.5 | 1000 | 45.24 | 31.58 | 600 | (0.61, 0.39) |
| Example 24 Organic electroluminescent device (14) | PO-01-TB-dipig | 4.2 | 1000 | 35.7 | 26.5 | 596 | (0.60, 0.40) |
| Com. Example 1 Conventional organic electroluminescent device | Ir(phq)$_2$acac | 4.4 | 1000 | 16.7 | 11.9 | 604 | (0.62, 0.37) |
| Com. Example 2 Conventional organic electroluminescent device | Ir(phq)$_2$acac | 4.3 | 1000 | 16.5 | 12.1 | 596 | (0.60, 0.40) |

It will be apparent to those skilled in the art that various modifications and variations can be made to the disclosed embodiments. It is intended that the specification and examples be considered as exemplary only, with the true scope of the disclosure being indicated by the following claims and their equivalents.

What is claimed is:

1. An organic metal complex represented by the following formula (I):

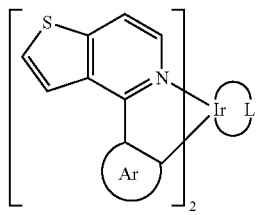

(I)

wherein,
Ar is 2-naphthyl, wherein the 2-naphthyl moiety is coordinated to iridium via the 3-position of the 2-naphthyl moiety; and
L is acetylacetone.

2. An organic electroluminescent device, comprising:
a pair of electrodes; and
an electroluminescent element disposed between the pair of electrodes, wherein the electroluminescent element comprises an organic metal complex represented by the following formula (I):

(I)

wherein,
Ar is 2-naphthyl, wherein the 2-naphthyl moiety is coordinated to iridium via the 3-position of the 2-naphthyl moiety; and
L is acetylacetone.

3. The organic electroluminescent device as claimed in claim 2, wherein the electroluminescent element emits reddish orange light or red light.

4. An organic metal complex represented by the following formula (II):

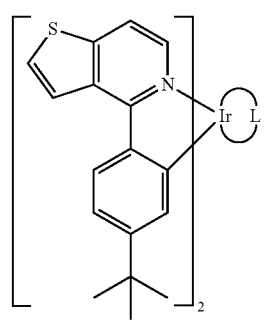

(II)

wherein,
L is N,N-diisopropyl-diisopropyl-guanidinate.

5. An organic electroluminescent device, comprising:
a pair of electrodes; and
an electroluminescent element disposed between the pair of electrodes, wherein the electroluminescent element comprises an organic metal complex represented by the following formula (II):

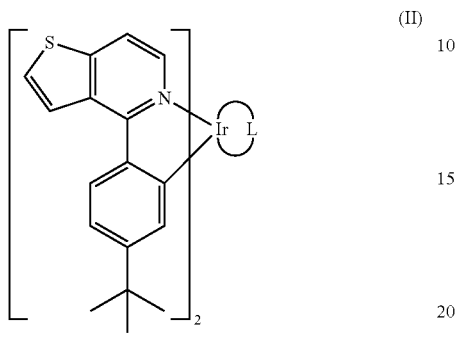

wherein L is N,N-diisopropyl-diisopropyl-guanidinate.

6. The organic electroluminescent device as claimed in claim 5, wherein the electroluminescent element emits reddish orange light or red light.

* * * * *